United States Patent [19]

Mauric et al.

[11] 4,220,472

[45] Sep. 2, 1980

[54] DIOXAPHOSPHORINANE DERIVATIVES AS FLAMEPROOFING AGENTS

[75] Inventors: Claudine Mauric, Basel; Rainer Wolf, Allschwil, both of Switzerland

[73] Assignee: Sandoz Ltd., Basle, Sweden

[21] Appl. No.: 598,198

[22] Filed: Jul. 23, 1975

[30] Foreign Application Priority Data

Jul. 30, 1974 [CH] Switzerland ............... 10463/74
May 26, 1975 [CH] Switzerland ............... 6720/75

[51] Int. Cl.$^2$ ............................................. C08K 5/51
[52] U.S. Cl. ........................... 106/18.18; 106/18.19; 260/45.8 R; 252/8.1; 260/927 R
[58] Field of Search ............... 260/461, 45.8 R, 927 R, 260/45.7 P; 252/8.1; 106/15 FP, 18.18, 18.19

[56] References Cited

U.S. PATENT DOCUMENTS

| | | | |
|---|---|---|---|
| 2,903,474 | 9/1959 | Lanham | 260/937 |
| 3,159,591 | 12/1964 | Lanham | 260/45.8 R |
| 3,597,511 | 8/1971 | Olson et al. | 260/45.8 R |
| 3,817,881 | 6/1974 | Turley | 260/45.7 P |
| 3,898,307 | 8/1975 | Mayerhoefer et al. | 260/45.7 P |
| 3,946,092 | 3/1976 | Nachbur et al. | 260/45.7 P |

FOREIGN PATENT DOCUMENTS 1020640 6/1958 Fed. Rep. of Germany .
770419 3/1957 United Kingdom .

OTHER PUBLICATIONS

Angew. Chem., Int. Ed. Vol. 6, pp. 1079–1080 (1967) Michalski et al.
Tetrahedron 1965 21 pp. 2379–2387.
Chem. Abs. 52 242f (1958).
Chem. Abs. 78 136244a (1973).
Chemistry and Industry—May 1963 pp. 784–785.
J. Phys. Chem. 75 No. 26 (1971) pp. 3975–3979.

Primary Examiner—V. P. Hoke
Attorney, Agent, or Firm—Gerald D. Sharkin; Richard E. Vila; Joseph J. Borovian

[57] ABSTRACT

Flameproofed polymeric organic materials, e.g. regenerated cellulose, which include bis-(2-oxo-1,3, 2-dioxaphosphorinanyl) oxides, bis-(2-thiono-1,3,2 -dioxaphosphorinanyl) oxides and 2-oxo-1,3,2-dioxaphosphorinanyl-2'-thiono-1',3',2'-dioxaphosphorinanyl oxides, having at least one substituent on the dioxaphosphorinane rings, as flameproofing agents, and their production. Some of the flameproofing agents are new compounds and are included in the invention.

11 Claims, No Drawings

DIOXAPHOSPHORINANE DERIVATIVES AS FLAMEPROOFING AGENTS

The present invention relates to flameproofed polymeric organic materials which include dioxaphosphorinane derivatives as flameproofing agents. More particularly, the flameproofing dioxaphosphorinane derivatives are chosen from bis-(2-oxo-1,3,2-dioxaphosphorinanyl)oxides, bis-(2-thiono-1,3,2-dioxaphosphorinanyl)oxides and 2-oxo-1,3,2-dioxaphosphorinanyl-2′-thiono-1′,3′,2′-dioxaphosphorinanyl oxides having at least one substituent on the dioxaphosphorinane rings.

Accordingly the present invention provides a flameproofed polymeric organic material including as a flameproofing agent a compound of formula I,

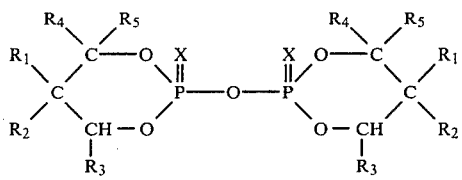

in which
each X, independently, is oxygen or sulphur,
each $R_1$, independently, is hydrogen, $C_1$-$C_4$ alkyl, chloromethyl, bromomethyl or phenyl,
each $R_2$, independently, is hydrogen, $C_1$-$C_4$ alkyl, chloromethyl or bromomethyl,
or $R_1$ and $R_2$, together with the carbon atom to which each is attached, on each dioxaphosphorinane ring independently, complete a cyclohexane, cyclohexene or 3,4-dibromocyclohexane ring,
each of $R_3$ and $R_5$, independently, is hydrogen or $C_1$-$C_4$ alkyl, and
each $R_4$, independently, is hydrogen or methyl,
with the provisos (i) that at least one of $R_1$, $R_2$, $R_3$, $R_4$ and $R_5$ from each dioxaphosphorinane ring is other than hydrogen, (ii) that when, on a dioxaphosphorinane ring, each of $R_1$ and $R_2$, independently, is chloromethyl or bromomethyl or $R_1$ and $R_2$ together with the carbon atom to which each is attached complete a ring, then each of $R_3$, $R_4$ and $R_5$ on that same dioxaphosphorinane ring is hydrogen, and (iii) when, on a dioxaphosphorinane ring, X is oxygen, then each of $R_1$ and $R_2$, independently, is chloromethyl or bromomethyl, or $R_1$ and $R_2$ together with the carbon atom to which each is attached, complete a ring.

In the above definition of formula I, it is to be understood that any alkyl radical represented by each $R_1$, $R_2$, $R_3$ and $R_5$, may be straight or branched chain when containing 3 or 4 carbon atoms, and thus may be n- or isopropyl or n-, iso- or tert.-butyl.

When either $R_1$ or either $R_2$ is alkyl, this preferably contains 1 to 3, more preferably 1 or 2 carbon atoms, and most preferably is methyl.

When either $R_1$ or either $R_2$ is chloro- or bromomethyl, this is preferably bromomethyl.

When either $R_1$ and $R_2$ bound to a common carbon atom complete a ring with that common carbon atom, this is preferably a cyclohexene or the 3,4-dibromocyclohexane ring.

Preferably both X's, simultaneously, are oxygen or sulphur, and more preferably, both X's are sulphur.

Each $R_1$ and $R_2$, independently, is preferably chloromethyl, bromomethyl, or, in the case when X on the same dioxaphosphorinane ring is sulphur, alkyl, or either $R_1$ and $R_2$, independently, together with the carbon atom to which each is attached, preferably complete a cyclohexane, cyclohexene or 3,4-dibromocyclohexane ring. More preferably, both $R_1$'s and both $R_2$'s simultaneously are chloromethyl, bromomethyl or, in the case when both X's simultaneously on the dioxaphosphorinane rings are sulphur, alkyl, or $R_1$ and $R_2$, together with the carbon atom to which each is attached, on both dioxaphosphorinane rings simultaneously, complete a cyclohexane, cyclohexene or 3,4-dibromocyclohexane ring. Most preferably, both $R_1$'s and both $R_2$'s simultaneously are chloromethyl, bromomethyl or alkyl.

Preferably each of the $R_3$'s, $R_4$'s and $R_5$'s, independently, is hydrogen.

The flameproofed polymeric organic material of the present invention preferably includes as a flameproofing agent a compound of formula Ia,

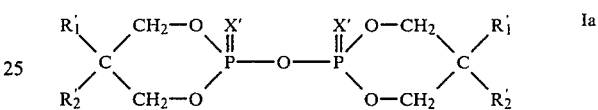

in which
both X″'s, simultaneously, are oxygen or sulphur,
and each $R_1'$ and each $R_2'$, independently, is chloromethyl, bromomethyl or additionally, in the case when the X″'s are sulphur, $C_1$-$C_4$ alkyl,
or $R_1'$ and $R_2'$, together with the carbon atom to which each is attached, on each dioxaphosphorinane ring independently, complete a cyclohexane, cyclohexene or 3,4-dibromocyclohexane ring.

More preferably, the flameproofing agent included in the flameproofed polymeric organic material is a compound of formula Ib,

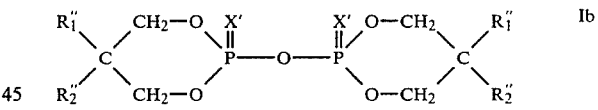

in which
both X″'s are oxygen or sulphur, and both $R_1'''$'s and both $R_2'''$'s, simultaneously, are bromomethyl, or, in the case when the X″'s are sulphur, each $R_1''$ and each $R_2''$, independently, is bromomethyl, chloromethyl, methyl, ethyl or propyl,
or $R_1''$ and $R_2''$, together with the carbon atom to which each is attached, on both dioxaphosphorinane rings simultaneously, complete a cyclohexene or 3,4-dibromocyclohexane ring.

Even more preferably, the flameproofing agent included in the flameproofed polymeric organic material is a compound of formula Ic,

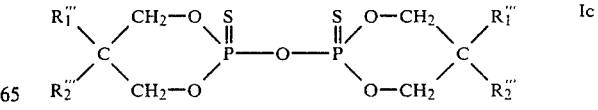

in which both $R_1''''$'s and both $R_2''''$'s simultaneously, are methyl, ethyl, chloromethyl or bromomethyl.

Most preferably, the flameproofed polymeric organic material of the present invention includes as a flameproofing agent a compound of formula Id,

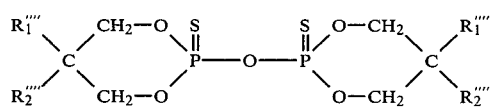

in which both $R_1''''$'s and both $R_2''''$'s, simultaneously, are methyl or bromomethyl.

The compounds of formula I',

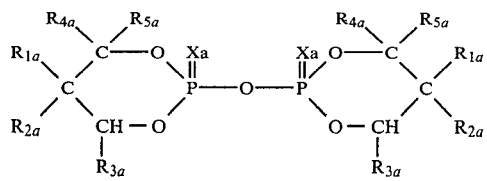

in which each of the Xa's, $R_{1a}$'s, $R_{2a}$'s, $R_{3a}$'s, $R_{4a}$'s, and $R_{5a}$'s, independently, has the meaning of each of the X's, $R_1$'s, $R_2$'s, $R_3$'s, $R_4$'s and $R_5$'s, respectively, given in the definition of formula I, above, the provisos (i), (ii) and (iii) given in that definition apply, and in addition with the proviso (iv) that when, on a dioxaphosphorinane ring, Xa is sulphur, $R_{1a}$ is methyl and $R_{2a}$ is hydrogen or methyl, then at least one of $R_{3a}$, $R_{4a}$ and $R_{5a}$ on that same dioxaphosphorinane ring is different from hydrogen, are new, and are also provided by the present invention.

The present invention further provides a process for the production of a compound of formula I', as defined above, which comprises hydrolysing one or two compounds of formula II,

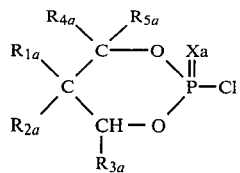

in which Xa, $R_{1a}$, $R_{2a}$, $R_{3a}$, $R_{4a}$ and $R_{5a}$ are as defined above,
with water in the presence of a base.

A suitable base of use in the process of the present invention is pyridine. It is to be understood that when one compound of formula II is used in the above process, the product is structurally symmetrical.

Intermediates of formula II, as defined above, may be produced in conventional manner from known starting materials or from starting materials produced by analogous processes to those for producing the known starting materials.

The particular compounds,

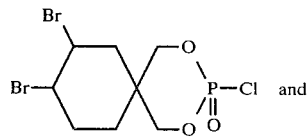 and

are new and also form part of the present invention. They may be produced in conventional manner by reacting phosphoryl or thiophosphoryl chloride, respectively, with 1,1-dihydroxymethyl-3,4-dibromocyclohexane, or by bromine addition on the corresponding 3,4-cyclohexene derivatives of the products, themselves known from German Pat. No. 1,051,279.

The compounds of formula I, other than those of formula I', may be produced in analogous manner to those of formula I' as described above.

In the flameproofed polymeric organic materials of the present invention, preferred organic materials rendered flameproofed by the inclusion of a compound of formula I, as defined above, are regenerated cellulose, polyolefins, e.g. polyethylene and polypropylene, polyesters, polyacrylic esters, e.g. polymethyl methacrylates, polyphenylene oxides, polyurethanes, polystyrene, polyamides, e.g. nylon, polypropylene oxide, polyacrylonitrile, copolymers of the aforementioned polymers, acrylonitrile-butadiene-styrene (ABS) terpolymers, and natural fibrous materials, e.g. cotton. More preferably, the organic materials are regenerated cellulose, polyethylene, polypropylene, polyesters, polyamides, copolymers of styrene and acrylonitrile and of styrene and butadiene, ABS-terpolymers and terpolymers of acrylic ester, styrene and acrylonitrile, and cotton of which regenerated cellulose is the most preferred.

The present invention further provides a method of producing a flameproofed polymeric organic material comprising treating the polymeric organic material directly or indirectly with a flameproofing-effective amount of a compound of formula I, as hereinbefore defined. Suitable polymeric organic materials which are flameproofed according to the method of the present invention include those mentioned above.

In this specification, by the term "treating" is meant either incorporating into the body of the polymeric organic material or surface coating such material, depending upon the substrate to be flameproofed.

The method may be carried out in a manner known per se, of which the following embodiments, which relate to the production of flameproofed polymeric organic materials other than regenerated cellulose and natural fibrous materials, are examples:

According to a first embodiment of the method of the present invention, the compound of formula I is mixed with a kneadable polymeric organic material, e.g. in particulate form, in a kneader or other suitable mixing device, to obtain the desired direct incorporation of the compound in the organic material. The latter may then be formed into the desired final shape, e.g. by extrusion into the form of, inter alia, films or fibres, or by injection moulding or spinning.

In a second embodiment, the compound of formula I is mixed with the appropriate monomer(s) and/or prepolymer before polymerisation or copolymerisation is effected, whereafter the polymerised product, with the compound distributed therethrough, may be extruded, injection moulded or otherwise formed into final shape.

This embodiment is particularly suitable for producing flameproofed polyurethanes and polyolefins, and illustrates the indirect incorporation of the compound in the organic material.

In a third embodiment, the compound of formula I is mixed with the polymeric organic material in molten form, after which the flameproofed material may be converted into the desired final shape e.g. by extrusion into, inter alia, films, injection moulding and spinning to produce fibres. This embodiment is particularly suitable for producing flameproofed polypropylene and provides a further illustration of direct incorporation.

The amount of flameproofing compound of formula I suitably incorporated into the polymeric organic material, other than regenerated cellulose and natural fibrous materials for imparting satisfactory flameproofing properties thereto will naturally depend on several factors, including the particular compound of formula I employed, the nature of the organic material to be flameproofed and the mode of incorporation. However, satisfactory results are generally obtained when the amount of compound employed is in the range 1 to 40%, preferably 2 to 10%, and more preferably 2 to 6%, of the weight of the polymeric organic material to be flameproofed.

The method of the present invention is particularly suitable for the production of flameproofed regenerated cellulose. In this case, the method comprises regenerating cellulose from its solution e.g. viscose, containing a compound of formula I, as defined above. Thus the regenerated cellulose produced has the compound incorporated therein and is flameproofed by virtue of its presence.

The term "regenerated cellulose" is well understood in the art to which it pertains. Amongst the procedures for producing regenerated cellulose are those involving the formation at one stage of alkali cellulose xanthate or a tetramine cupric hydroxide complex of cellulose, and such procedures are so adapted according to this embodiment of the method to include the regeneration of cellulose from its solution containing the compound of formula I as a flameproofing agent.

Prior to the regeneration, cellulose is brought into solution, e.g. by such known processes as converting it into a soluble derivative by the xanthate method or through formation of the tetramine cupric hydroxide complex thereof. The compound of formula I is then added to the cellulose solution, for example by itself or as a fine dispersion in water. When added alone, the compound may be introduced into the cellulose solution either continuously or discontinuously, i.e. in batches, and thereafter vigorous stirring of the cellulose solution containing the compound may be applied to distribute it uniformly in the solution. The same technique may also be adopted for the addition of an aqueous dispersion of the compound. Preferably the weight of compound of formula I present in the cellulose solution from which flameproofed regenerated cellulose is to be produced is in the range 5 to 35% of the weight of the cellulose starting material, e.g. α-cellulose, or more preferably 10 to 25% of its weight. In all cases it can be advantageous to add conventional dispersion stabilisers and/or dispersion agents to the cellulose medium to promote uniformity of distribution of the compound in the cellulose solution.

Other flameproofing compounds, e.g. reaction products of a phosphorus nitrile chloride with glycols e.g. neopentylglycol or other glycols, as described in German Offenlegungsschrift No. 2,316,959, or cyclodiphosphazanes or thionocyclodiphosphazanes, as described in German Offenlegungsschrift No. 2,451,802, may be added to the cellulose solution as well as a compound of formula I. The amount of such additional flameproofing agents when employed may be up to 90% by weight of the total flameproofing agent present in the cellulose solution. In the case of reaction products of a phosphorus nitrile chloride and a glycol, cyclodiphosphazane and thionocyclodiphosphazane, such auxiliary flameproofing agent preferably constitutes 10 to 70%, or more preferably 15 to 60%, of the total weight of flameproofing agent in the solution.

The regenerated cellulose is produced in shaped form from the solution in conventional manner by forcing the solution into a precipitation bath through fine nozzles or slots, thereby producing filaments or sheets, respectively. Apart from flame resistance, the so-produced flameproofed regenerated cellulose possesses its normal technically important properties which are only slightly affected by the presence of the incorporated flameproofing agent.

Natural fibrous materials are treated, according to the method of the present invention, by coating the compound of formula I, suitably present in a coating liquor, onto the substrate. Thus the material is treated directly with the compound of formula I. Where blend fabrics of synthetic and/or semi-synthetic and natural fibrous organic materials e.g. polyester-cotton blend fabrics, are to be flameproofed, the synthetic or semisynthetic organic material may be independently treated according to the method of the invention, e.g. as described in the above embodiments, and then blended with the natural fibrous organic material, the blend fabric then being optionally further treated with a compound of formula I by coating if a higher degree of flameproofing is necessary or desired. Alternatively, the untreated blend fabric may be treated with the compound by coating.

The present invention is illustrated by the following Examples, in which the parts and percentages are by weight.

EXAMPLE 1

To a solution of 338.8 parts of thiophosphoryl chloride in 3000 parts of benzene are added 314.4 parts of pyridine at 20° C. followed by 523.9 parts of 2,2-bis(-bromomethyl)-1,3-propanediol at 20° to 35° C. over a period of 30 minutes. The mixture is then stirred at 50° C. for 24 hours, cooled to 20° C., and filtered. On evaporation of the filtrate in vacuo, 743 parts of impure 2-chloro-2-thio-5,5-bis(bromomethyl)-1,3,2-dioxaphosphorinane, of formula,

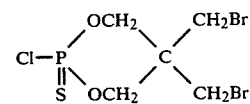

are obtained. Recrystallisation from carbon tetrachloride results in a purer product, m.p. 106°–108° C.

To a solution of 71.7 parts of the above intermediate in 136 parts of tetrahydrofuran are added to 16.3 parts of pyridine and 1.8 parts of water. The mixture is stirred at a reflux temperature for 4 hours. After the completion of the reaction the mixture is cooled to 20° C. and 300 parts of ethyl acetate are added. The mixture is washed with water and after concentration of the organic phase 38 parts of a compound of the formula,

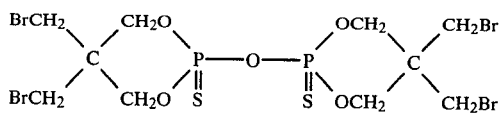

having a melting point of 190°-192° crystallise out. Crystallisation from benzene results in a purer product m.p. 198°-199° C.

This is a new compound and forms part of the present invention.

EXAMPLES 2 to 18

The following compounds are produced in an analogous manner to that described in Example 1.

| Example | Structure | Melting Point (°C.) |
|---|---|---|
| 2 | $\left\{\begin{array}{c}BrCH_2\\ BrCH_2\end{array}\!\!>\!\!C\!\!<\!\!\begin{array}{c}CH_2O\\ CH_2O\end{array}\!\!>\!\!P(\!=\!O)\!-\!O\right\}_2$ | 174°-175° |
| 3 | $\left\{\begin{array}{c}CH_3\\ CH_3\end{array}\!\!>\!\!C\!\!<\!\!\begin{array}{c}CH_2O\\ CH_2O\end{array}\!\!>\!\!P(\!=\!S)\!-\!O\right\}_2$ | 228°-229° |
| 4 | $\left\{\begin{array}{c}ClCH_2\\ ClCH_2\end{array}\!\!>\!\!C\!\!<\!\!\begin{array}{c}CH_2O\\ CH_2O\end{array}\!\!>\!\!P(\!=\!S)\!-\!O\right\}_2$ | 199°-200° |
| 5 | $\left\{\begin{array}{c}CH_3\\ C_2H_7\end{array}\!\!>\!\!C\!\!<\!\!\begin{array}{c}CH_2O\\ CH_2O\end{array}\!\!>\!\!P(\!=\!S)\!-\!O\right\}_2$ | 134°-136° |
| 6 | $\left\{\begin{array}{c}C_2H_5\\ C_2H_5\end{array}\!\!>\!\!C\!\!<\!\!\begin{array}{c}CH_2O\\ CH_2O\end{array}\!\!>\!\!P(\!=\!S)\!-\!O\right\}_2$ | 139°-140° |
| 7 | $\left\{\begin{array}{c}CH_3\\ C_3H_7\end{array}\!\!>\!\!C\!\!<\!\!\begin{array}{c}CH_2O\\ CH_2O\end{array}\!\!>\!\!P(\!=\!S)\!-\!O\right\}_2$ | 139°-141° |
| 8 | $\left\{\begin{array}{c}C_2H_5\\ n\text{-}C_2H_9\end{array}\!\!>\!\!C\!\!<\!\!\begin{array}{c}CH_2O\\ CH_2O\end{array}\!\!>\!\!P(\!=\!S)\!-\!O\right\}_2$ | -(liquid) |
| 9 | $\left\{\begin{array}{c}CH_3\\ C_6H_5\end{array}\!\!>\!\!C\!\!<\!\!\begin{array}{c}CH_2O\\ CH_2O\end{array}\!\!>\!\!P(\!=\!S)\!-\!O\right\}_2$ | 240°-242° |
| 10 | $\left\{\begin{array}{c}HC\!\!\equiv\!\!C\!-\!CH_2\\ CH_2\!-\!CH_2\end{array}\!\!>\!\!C\!\!<\!\!\begin{array}{c}CH_2O\\ CH_2O\end{array}\!\!>\!\!P(\!=\!S)\!-\!O\right\}_2$ | 187°-188° |
| 11 | $\left\{\begin{array}{c}Br\!-\!CH\!=\!CH\!-\!CH_2\\ CH_2\!-\!CH_2\end{array}\!\!>\!\!C\!\!<\!\!\begin{array}{c}CH_2O\\ CH_2O\end{array}\!\!>\!\!P(\!=\!S)\!-\!O\right\}_2$ | 228° with decomposition |
| 12 | $\left\{\begin{array}{c}CH_3\\ CH_3\end{array}\!\!>\!\!C\!\!<\!\!\begin{array}{c}CH_2O\\ CHO(n\text{-}C_3H_7)\end{array}\!\!>\!\!P(\!=\!S)\!-\!O\right\}_2$ | 106°-108° |

-continued

| Example | Structure | Melting Point (°C.) |
|---------|-----------|---------------------|
| 13 | (structure) | 157°–158° |
| 14 | (structure) | –(liquid) |
| 15 | (structure) | 159°–160° |
| 16 | (structure) | 161°–163° |
| 17 | (structure) | 239°–241° |
| 18 | (structure) | 140° with decomposition |

All the compounds except that of Example 3 are new, and so form part of the present invention.

In the case of the production of the compounds of Examples 2, 17 and 18, phosphoryl chloride is used instead of thiophosphoryl chloride, as in the remaining Examples, as a starting material. In many cases it is unnecessary to use pyridine and benzene in the production of the intermediate substituted 2-chloro-2-oxy or thio-1,3,2-dioxaphosphorinane. For the production of the final product from the aforementioned intermediate an excess of pyridine instead of a solvent such as tetrahydrofuran, as in Example 1, may be used in many cases.

The mode of isolation of a reaction product from the reaction mixture is dependent on the solubility and the state of aggregation of the particular compound. If precipitated during the reaction, the compound may be collected by filtration and washed with water. However, if it remains dissolved in the reaction liquor, its precipitation therefrom may be induced by addition of a diluent such as water. In the case of a product normally in a liquid state, such as the compounds of Examples 8 and 14, it is generally appropriate to filter the reaction mixture, concentrate the filtrate in vacuo, dissolve the residue in diethyl ether, wash the etheral solution with water, remove the ether solvent by evaporation in vacuo and distil the oil residue, removing volatile impurities at about 50° C. at less than 0.1 mm. of mercury pressure.

As well as by hydrolysing the appropriate 5,5-substituted-2-chloro-2-oxy or thio-1,3,2-dioxaphosphorinane, the compounds of Examples 11 and 18 may also be obtained by brominating the compounds of Examples 10 and 17, respectively.

APPLICATION EXAMPLE 1

A 22% aqueous dispersion of the compound of Example 3 is prepared as follows: 50 parts of the compound of Example 3 are ground to a powder during 3 hours with 12.5 parts of a dispersing agent based on sodium naphthalenesulphonate and 137.5 parts of water by revolution at the rate of 1500 revolutions per minute in the presence of 200 parts of quartzite beads, cooling with ice being maintained throughout the grinding. The quartzite beads are then removed by filtration and 180 parts of a dispersion containing 22% of the compound are obtained.

16.4 Parts of the 22% aqueous dispersion are introduced with stirring into 200 parts of a cellulose xanthate solution prepared from 18 parts of α-cellulose. The solution is forced through nozzles by a conventional spinning process into a precipitation bath containing 125 g of sulphuric acid, 240 g of anhydrous sodium sulphate and 12 g of anhydrous zinc sulphate per liter. The resulting fibres are washed thoroughly and formed into knit fabrics which are subsequently tested for flame-resistance by the method of Fenimore and Martin, described in Modern Plastics, November 1966, involving the determination of the oxygen limit value (LOI). Comparison of the results with those given by untreated regenerated cellulose indicates the flameproofing property imparted by the incorporated compound of Example 3.

Similarly the compounds of Examples 1, 2, 4 to 7, 9 to 13 and 15 to 18 may be used for flameproofing regenerated cellulose.

APPLICATION EXAMPLE 2

3.6 Parts of the compound of Example 8 are introduced with stirring into 200 parts of a cellulose xanthate solution prepared from 18 parts of α-cellulose. The ensuing production and testing of the flameproofed cellulose is effected as described in Application Example 1.

APPLICATION EXAMPLE 3

8.2 Parts of a 22% aqueous dispersion of the compound of Example 3 (produced as described in Application Example 1) and 9 parts of a 22% aqueous dispersion of 2,4-dianilino-2,4-dioxa-1,3-cyclodiphosphazane are successively stirred into 200 parts of a cellulose xanthate solution prepared from 18 parts of α-cellulose. The ensuing production and testing of the flameproofed cellulose is effected as described in Application Example 1.

APPLICATION EXAMPLE 4

3 Parts of the compound of Example 2 are well mixed with 100 parts of polypropylene powder (Propathene HM 20, obtainable from Imperial Chemical Industries) in a shaking machine and the mixture is then formed into a sheet on a "roller seat" for 5 minutes at 165° to 175° C. After comminution the sheet is compressed at 220° C. at pressures of 1.5 atm. for 1.5 minutes and 30 atm. for 1.5 minutes. The sheets obtained are tested by the DIN 53438 and LOI methods.

What is claimed is:

1. A flameproofed polymeric organic material containing, as a flameproofing agent, a flameproofing effective amount of a compound of the formula, $$\begin{array}{c} R_4 \\ R_1 \\ \diagdown \\ R_2 \end{array} \begin{array}{c} R_5 \\ C-O \\ \diagup \\ CH-O \\ | \\ R_3 \end{array} \begin{array}{c} S \\ \diagdown \\ P-O-P \\ \diagup \end{array} \begin{array}{c} S \\ \diagdown \\ O-CH \\ | \\ R_3 \end{array} \begin{array}{c} R_4 \\ R_5 \\ \diagup \\ C \\ \diagdown \\ R_2 \end{array}$$

in which
each $R_1$, independently, is hydrogen, $C_1-C_4$ alkyl, chloromethyl, bromomethyl or phenyl,
each $R_2$, independently, is hydrogen, $C_1-C_4$ alkyl, chloromethyl or bromomethyl,
or $R_1$ and $R_2$, together with the carbon atom to which each is attached, on each dioxaphosphorinane ring independently, complete a cyclohexane, cyclohexene or 3,4-dibromocyclohexane ring,
each of $R_3$ and $R_5$, independently, is hydrogen or $C_1-C_4$ alkyl,
and each $R_4$, independently, is hydrogen or methyl, with the provisos (i) that at least one of $R_1$, $R_2$, $R_3$, $R_4$ and $R_5$ from each dioxaphosphorinane ring is other than hydrogen, and (ii) that when, on a dioxaphosphorinane ring, each of $R_1$ and $R_2$, independently, is chloromethyl or bromomethyl, or $R_1$ and $R_2$ together with the carbon atom to which each is attached complete a ring, then each of $R_3$, $R_4$ and $R_5$ on that same dioxaphosphorinane ring is hydrogen.

2. A flameproofed polymeric organic material according to claim 1 containing, as a flameproofing agent, a compound of the formula, $$\begin{array}{c} R_1' \\ \diagdown \\ R_2' \end{array} \begin{array}{c} CH_2-O \\ \diagup \\ CH_2-O \end{array} \begin{array}{c} S \\ \diagdown \\ P-O-P \\ \diagup \end{array} \begin{array}{c} S \\ \diagdown \\ O-CH_2 \\ \diagup \\ O-CH_2 \end{array} \begin{array}{c} R_1' \\ \diagup \\ C \\ \diagdown \\ R_2' \end{array}$$

in which
each $R_1'$ and each $R_2'$, independently, is $C_1-C_4$ alkyl, chloromethyl or bromomethyl,
or $R_1'$ and $R_2'$, together with the carbon atom to which each is attached, on each dioxaphosphorinane ring independently, complete a cyclohexane, cyclohexene or 3,4-dibromocyclohexane ring.

3. A flameproofed polymeric organic material according to claim 2 containing, as a flameproofing agent, a compound of the formula, $$\begin{array}{c} R_1'' \\ \diagdown \\ R_2'' \end{array} \begin{array}{c} CH_2-O \\ \diagup \\ CH_2-O \end{array} \begin{array}{c} S \\ \diagdown \\ P-O-P \\ \diagup \end{array} \begin{array}{c} S \\ \diagdown \\ O-CH_2 \\ \diagup \\ O-CH_2 \end{array} \begin{array}{c} R_1'' \\ \diagup \\ C \\ \diagdown \\ R_2'' \end{array}$$

in which
each $R_1''$ and each $R_2''$, independently, is methyl, ethyl, propyl, chloromethyl or bromomethyl,
or $R_1''$ and $R_2''$, together with the carbon atom to which each is attached, on each dioxaphosphorinane ring, complete a cyclohexene or 3,4-dibromocyclohexane ring,
with the proviso that when $R_1''$ and $R_2''$ and the attached carbon atom, on both dioxaphosphorinane rings, complete a cyclohexene or 3,4-dibromocyclohexane ring, both rings are identical.

4. A flameproofed polymeric organic material according to claim 1, in which the polymeric organic material is selected from regenerated cellulose, polyolefins, polyesters, polyacrylic esters, polyphenylene oxides, polyurethanes, polystyrene, polyamides, polypropylene oxide, polyacrylonitrile, copolymers of the aforementioned polymers, acrylonitrile-butadienestyrene terpolymers, and natural fibrous materials.

5. A flameproofed polymeric organic material according to claim 4, in which the polymeric organic material is regenerated cellulose.

6. A flameproofed polymeric organic material according to claim 3 containing, as a flameproofing agent, a compound of the formula, $$\begin{array}{c} R_1''' \\ \diagdown \\ R_2''' \end{array} \begin{array}{c} CH_2-O \\ \diagup \\ CH_2-O \end{array} \begin{array}{c} S \\ \diagdown \\ P-O-P \\ \diagup \end{array} \begin{array}{c} S \\ \diagdown \\ O-CH_2 \\ \diagup \\ O-CH_2 \end{array} \begin{array}{c} R_1''' \\ \diagup \\ C \\ \diagdown \\ R_2''' \end{array}$$

in which each $R_1'''$ and each $R_2'''$ is bromomethyl, chloromethyl, methyl or ethyl, the $R_1''''$'s and $R_2''''$'s being identical.

7. A flameproofed polymeric organic material according to claim 6 containing, as a flameproofing agent, a compound of the formula,

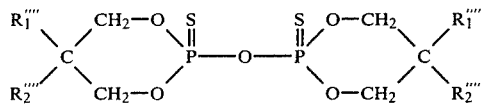

in which each $R_1''''$ and each $R_2''''$ is bromomethyl or methyl, the $R_1''''$'s and $R_2''''$'s being identical.

8. A flameproofed polymeric organic material according to claim 7 containing, as a flameproofing agent, a compound of the formula,

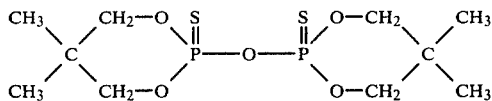

9. A method of producing a flameproofed polymeric organic material comprising treating the polymeric organic material with a flameproofing effective amount of a compound of the formula,

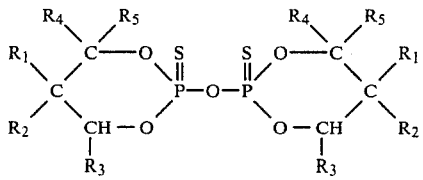

in which
each $R_1$, independently, is hydrogen, $C_1$–$C_4$ alkyl, chloromethyl, bromomethyl or phenyl,
each $R_2$, independently, is hydrogen, $C_1$–$C_4$ alkyl, chloromethyl or bromomethyl,
or $R_1$ and $R_2$, together with the carbon atom to which each is attached, on each dioxaphosphorinane ring independently, complete a cyclohexane, cyclohexene or 3,4-dibromocyclohexane ring,
each of $R_3$ and $R_5$, independently, is hydrogen or $C_1$–$C_4$ alkyl,
and each $R_4$, independently, is hydrogen or methyl, with the provisos (i) that at least one of $R_1$, $R_2$, $R_3$, $R_4$ and $R_5$ from each dioxaphosphorinane ring is other than hydrogen, and (ii) that when, on a dioxaphosphorinane ring, each of $R_1$ and $R_2$, independently, is chloromethyl or bromomethyl, or $R_1$ and $R_2$ together with the carbon atom to which each is attached complete a ring, then each of $R_3$, $R_4$ and $R_5$ on that same dioxaphosphorinane ring is hydrogen.

10. A method according to claim 9, in which the polymeric organic material is selected from regenerated cellulose, polyolefins, polyesters, polyacrylic esters, polyphenylene oxides, polyurethanes, polystyrene, polyamides, polypropylene oxide, polyacrylonitrile, copolymers of the aforementioned polymers, acrylonitrile-butadienestyrene terpolymers, and natural fibrous materials.

11. A method according to claim 10, in which the polymeric organic material is regenerated cellulose.

* * * * *